United States Patent
Camps et al.

(10) Patent No.: US 7,801,622 B2
(45) Date of Patent: Sep. 21, 2010

(54) MEDICAL ELECTRICAL LEAD AND DELIVERY SYSTEM

(75) Inventors: Antoine N. J. M. Camps, Eys (NL); Ron Van Der Kruk, Bunde (NL); Jean J. G. Rutten, Bocholtz (NL)

(73) Assignee: Medtronic, Inc., Minneapolis, MN (US)

( * ) Notice: Subject to any disclaimer, the term of this patent is extended or adjusted under 35 U.S.C. 154(b) by 272 days.

(21) Appl. No.: 11/393,239

(22) Filed: Mar. 30, 2006

(65) Prior Publication Data

US 2007/0239246 A1 Oct. 11, 2007

(51) Int. Cl.
*A61N 1/372* (2006.01)

(52) U.S. Cl. .................................................. 607/116

(58) Field of Classification Search ............... 607/127, 607/131, 116
See application file for complete search history.

(56) References Cited

U.S. PATENT DOCUMENTS

| | | | | |
|---|---|---|---|---|
| 3,516,412 | A * | 6/1970 | Ackerman | 607/125 |
| 4,357,946 | A | 11/1982 | Dutcher | |
| 5,342,414 | A | 8/1994 | Mehra | |
| 5,534,022 | A | 7/1996 | Hoffman et al. | |
| 5,571,163 | A * | 11/1996 | Helland | 607/123 |
| 6,253,110 | B1 | 6/2001 | Brabec et al. | |
| 6,687,550 | B1 * | 2/2004 | Doan | 607/127 |
| 6,813,521 | B2 * | 11/2004 | Bischoff et al. | 607/122 |
| 6,837,848 | B2 | 1/2005 | Bonner et al. | |
| 6,890,295 | B2 * | 5/2005 | Michels et al. | 600/114 |
| 6,915,169 | B2 * | 7/2005 | Flynn et al. | 607/122 |
| 6,918,908 | B2 | 7/2005 | Bonner et al. | |
| 7,033,326 | B1 * | 4/2006 | Pianca et al. | 600/585 |
| 2004/0064173 | A1 | 4/2004 | Hine et al. | |
| 2004/0088035 | A1 | 5/2004 | Guenst et al. | |
| 2004/0147994 | A1 * | 7/2004 | Zhang et al. | 607/127 |
| 2005/0131511 | A1 | 6/2005 | Westlund | |
| 2006/0235499 | A1 * | 10/2006 | Heil et al. | 607/127 |

OTHER PUBLICATIONS

International Search Report, PCT/US2007/064261, Jun. 22, 2007, 5 Pages.

* cited by examiner

*Primary Examiner*—Scott M Getzow
*Assistant Examiner*—Amanda Patton
(74) *Attorney, Agent, or Firm*—Stephen W. Bauer (57) ABSTRACT

A medical electrical lead having an elongated lead body extending from a proximal end to a distal end, a first electrode positioned at the distal end of the lead body, a second electrode spaced proximally from the first electrode, the second electrode being a flexible conductive coil and having a distal end. A first electrode sleeve is coupled to the first electrode, and a second electrode sleeve is coupled to the second electrode and positioned within the proximal end of the lead body and proximal the distal end of the second electrode to provide flexibility in a distal lead body portion.

20 Claims, 7 Drawing Sheets

MEDICAL ELECTRICAL LEAD AND DELIVERY SYSTEM

CROSS-REFERENCE TO RELATED APPLICATION

Cross-reference is hereby made to commonly-assigned related U.S. application Ser. No. 11/393,354, filed concurrently herewith, entitled "MEDICAL ELECTRICAL LEAD AND DELIVERY SYSTEM".

TECHNICAL FIELD

The invention relates generally to implantable medical devices and, in particular, to a medical electrical lead and medical lead delivery system.

BACKGROUND

Implantable medical device (IMD) systems used for monitoring cardiac signals or delivering electrical stimulation therapy often employ electrodes implanted in contact with the heart tissue. Such electrodes may be carried by transvenous leads to facilitate implantation at endocardial sites or along a cardiac vein. Epicardial leads, on the other hand, carry electrodes adapted for implantation at an epicardial site. In past practice, placement of transvenous leads is often preferred by a physician over epicardial lead placement since transvenous leads can be advanced along a venous path in a minimally invasive procedure. Epicardial lead placement has generally required a sternotomy in order to expose a portion of the heart to allow implantation of the epicardial electrode at a desired site.

However, depending on the particular application, an epicardial lead may provide better therapeutic results than a transvenous lead. For example, in cardiac resynchronization therapy (CRT), a transvenous lead is advanced through the coronary sinus into a cardiac vein over the left ventricle. Implantation of a transvenous lead in a cardiac vein site can be a time-consuming task and requires considerable skill by the implanting clinician due to the small size and tortuosity of the cardiac veins. Furthermore, implant sites over the left heart chambers are limited to the pathways of the accessible cardiac veins when using a transvenous lead, which does not necessarily correspond to therapeutically optimal stimulation sites. Epicardial electrodes are not restricted to the pathways of the cardiac veins and can be implanted over any part of the heart surface. In order to take full advantage of cardiac stimulation therapies such as CRT, it is desirable to offer a cardiac lead that can be implanted in an epicardial location and a delivery system that allows the lead to be implanted using a generally less invasive approach, such as a mini-thoracotomy or thorascopic approach, than a full sternotomy.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise noted, elements shown in the drawings are not drawn to scale.

Figure 1:
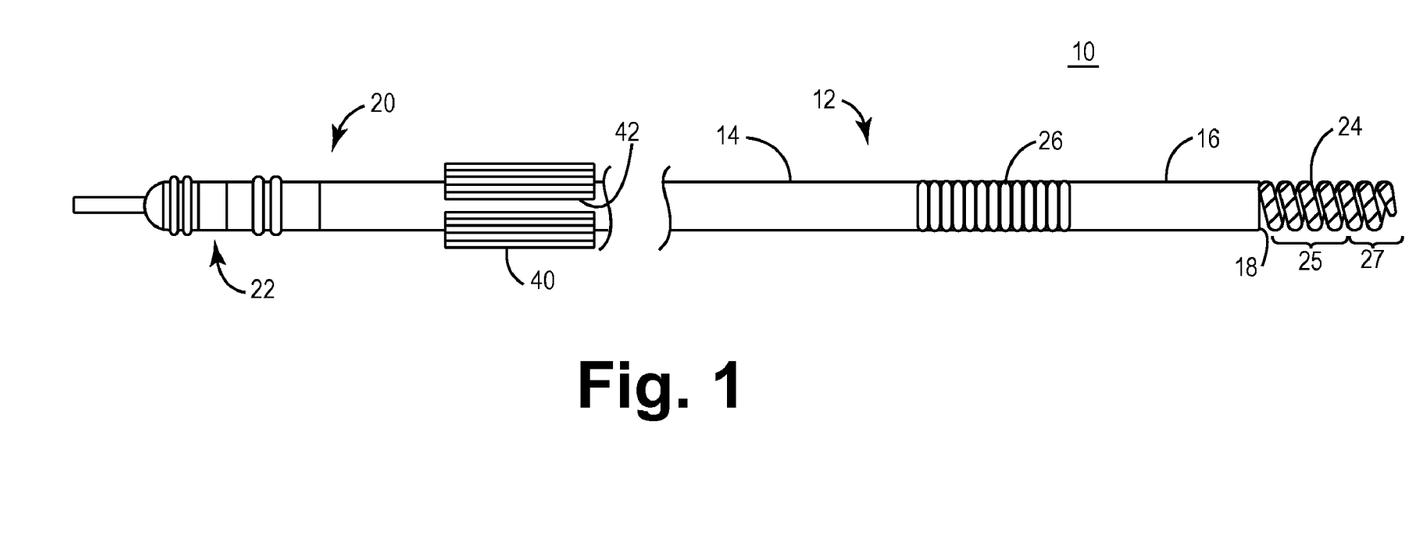
FIG. 1 is a plan view of a medical electrical lead in accordance with one embodiment of the invention.

FIG. 1 is a plan view of a medical electrical lead in accordance with one embodiment of the invention. Lead 10 is adapted for implantation at epicardial locations, but may also be implanted transvenously in endocardial locations, including positions along the coronary sinus and cardiac veins. Lead 10 is a bipolar lead provided for sensing cardiac signals and delivering bipolar electrical stimulation pulses to the heart. In other embodiments, lead 10 may be provided as a unipolar lead or a multipolar lead. Lead 10 includes an elongated lead body 12 having a proximal end 20 and a distal end 18. In one embodiment, a tip electrode 24 is provided as an active fixation electrode positioned at the distal end 18 of lead 10. Tip electrode 24 is shown as a "screw-in" helical electrode and is used as the cathode electrode during bipolar stimulation. Helical tip electrode 24 is generally provided with a length that is relatively longer than helical tip electrodes carried by conventional transvenous leads. For example, a conventional transvenous helical tip electrode is commonly provided with a length of about 2 mm. In one embodiment of the present invention, tip electrode 24 is provided with a helix length greater than about 2 mm, for example a length of about 4 mm, to promote reliable fixation of the electrode 24 at an implant site. The increased length of tip electrode 24 reduces the likelihood of lead dislodgement, particularly from epicardial implant sites. It is recognized that in alternative embodiments, the tip electrode 24 may be provided as other types of electrodes, such as a generally hemispherical electrode with passive fixation members provided at distal lead end 18.

Tip electrode 24 is formed from a helically wound conductive material, such as platinum, iridium or alloys thereof. The helical windings of tip electrode 24 are formed with a relatively small pitch angle to further promote reliable fixation of electrode 24 within the myocardial tissue. A larger winding pitch may allow electrode 24 to more easily rotate back out of the myocardial tissue. For example, tip electrode 24 may be formed with a winding pitch less than about 22 degrees. In one embodiment, tip electrode 24 is formed with a winding pitch of about 17 degrees, though it is recognized that other angles may be used successfully for promoting reliable fixation of electrode 24 in the cardiac tissue without causing undue tissue compression between the windings.

By providing both a longer helix with a small winding pitch, a greater total linear length of the tip electrode 24 interacts with the myocardial tissue for promoting reliable fixation of lead 10. Stresses imposed on tip electrode 24 are distributed along a greater length of material and are potentially reduced by providing a low winding pitch, potentially extending the functional life of tip electrode 24.

However, the greater surface area of tip electrode 24 exposed to myocardial tissue may reduce the electrical performance of electrode 24 since the delivered pulse energy will be spread over a larger electrode-tissue interface, potentially resulting in higher pulse energy required for capturing the heart tissue. Using higher pulse energies for stimulating the heart will result in earlier battery depletion of the implantable device coupled to lead 10. As such, tip electrode 24 may be provided with an insulating coating on proximal windings 25, with one or more distal windings 27 remaining exposed and serving as the active electrode. Appropriate insulating coatings include silicone, polyurethane, polyimide, or non-conductive or high impedance (>50 kohm) metal coatings. By insulating proximal windings 25, the electrically active surface of tip electrode 24 interfacing with myocardial tissue is effectively reduced, which improves the electrical performance of tip electrode 24. As such, a helical electrode having a relatively long length and/or small winding pitch may be used to improve fixation of electrode 24 in the myocardial tissue without sacrificing desired electrical performance of electrode 24.

An anode electrode 26 is spaced proximally from the tip electrode 24 and is provided as a flexible electrode formed from a coiled conductive wire, cable, or multifilar conductor. When tip electrode 24 is fixed in the cardiac tissue, considerable flexion of lead 10 in the vicinity of the heart will occur due to heart motion. Accordingly, anode electrode 26 is provided as a flexible electrode able to withstand the constant motion imparted on lead 10 by the heart, without dislodgement or fracture of lead components. The desired flexibility of anode electrode 26 is achieved by selecting the material, thickness (or number of filars), cross-sectional shape (e.g., circular, oval, flat, reqtangular etc.) and pitch of the conductive wire, cable or multifilar conductor used to form anode electrode 26. In one embodiment, anode electrode 26 is formed from a bifilar coil.

Tip electrode 24 and/or anode electrode 26 may be coated with titanium nitride (TiN) or another coating, such as platinum black, ruthenium oxide, iridium oxide, carbon black, or other metal oxides or metal nitrides, to reduce post-pace polarization. Reference is made, for example, to U.S. Pat. No. 6,253,110 (Brabec, et al.), hereby incorporated herein by reference in its entirety. During the coating process, flexible anode electrode 26 is held in a stable position by a mandrel to promote even application of the coating.

Lead body 12 includes a proximal portion 14 extending between anode electrode 26 and a proximal connector assembly 22 and a distal portion 16 extending between anode electrode 26 and tip electrode 24. In one embodiment, distal body portion 16 is formed from a more flexible material than proximal body portion 14. Distal body portion 16 is subjected to greater flexion due to heart motion than proximal body portion 14. Accordingly, distal body portion 16 is provided with greater flexibility to withstand the substantially continuous motion imparted on lead 10 by the heart. Proximal portion 14, extending to proximal connector assembly 22 is formed from a stiffer material that provides the torsional resistance needed for allowing rotation of lead body 12 during advancement of tip electrode 24 into the myocardial tissue. It is desirable for example, to provide proximal portion 14 with a torsional stiffness that results in an approximately 1:1 torque transfer from proximal lead body end 20 to distal lead body end 18. In one embodiment distal portion 16 is formed from silicone rubber and proximal portion 14 is formed from polyurethane. In another embodiment distal portion 16 is formed from polyurethane having a lower durometer than the polyurethane used to form proximal portion 14. In still another embodiment, distal portion 16 and proximal portion 14 are formed from the same material but distal portion 16 is formed having a thinner wall thickness than proximal portion 14.

Rotation of lead body 12 may be facilitated by a rotation sleeve 40 adapted to be positioned around proximal lead body portion 14 near proximal end 20. Rotation sleeve 40 is a generally cylindrical member, typically formed from plastic, such as silicone rubber or polyurethane, and having an open side 42 which may be widened to allow rotation sleeve 40 to be placed over lead body 12. Rotation sleeve 40 enables the implanting physician to more easily grip and rotate lead 10 during an implantation procedure. Rotation sleeve 40 is removed from lead body 12 after lead 10 is implanted.

Figure 2:
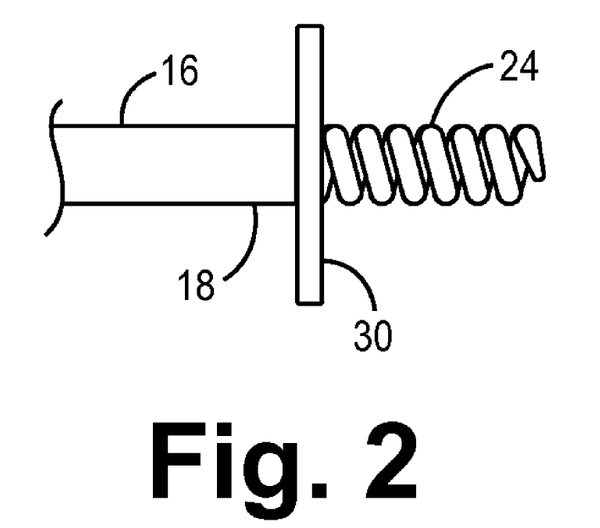
FIG. 2 is a plan view of the distal lead end of a medical electrical lead according to one embodiment of the invention.

FIG. 2 is a plan view of the distal lead end of a medical electrical according to one embodiment of the invention. In past practice, epicardial leads are often provided with a suture pad or other feature for accommodating the placement of anchoring sutures for stabilizing the position of the lead at the epicardial implant site. In one embodiment, the present invention is directed to an epicardial lead system that can be implanted via a mini thoracotomy, thoracoscopy, or sub-xiphoid approach. In order to minimize the invasiveness of the procedure, a small incision is made, limiting the open view and access to the epicardium and restricting the ability of the implanting physician to place anchoring sutures. In FIG. 2, an optional stabilizing member 30 is provided for promoting tissue adhesion to the distal lead body end 18 for stabilizing the lead position on the myocardial tissue, without requiring the use of anchoring sutures. Stabilizing member 30 is provided as a Dacron mesh or other medical grade material that promotes tissue ingrowth or adhesion. Stabilizing member 30 may be formed from a biodegradable material, such as a collagen-based material, to promote fixation of distal lead body end 18 during the acute phase. Stabilizing member 30 is provided as a generally flat piece of material extending radially from distal lead body portion 16. Stabilizing member is positioned near distal lead body end 18 such that it will substantially rest against the epicardium when tip electrode 24 is advanced into the epicardium.

Figure 3:
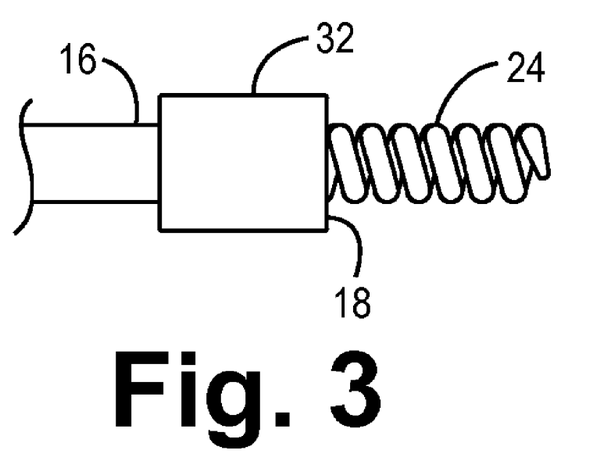
FIG. 3 is a plan view of an alternative embodiment of a medical electrical lead including a stabilizing member.

FIG. 3 is a plan view of an alternative embodiment of a medical electrical lead including a stabilizing member. Stabilizing member 32 is formed of Dacron mesh or other medical grade material for promoting tissue ingrowth or adhesion for stabilizing the position of distal lead end 18 implanted through the epicardial surface of the heart, in a partially transmural position in the myocardium. As will be described in greater detail below, lead 10 shown in FIG. 1 may be implanted in an epicardial position such that tip electrode 24 is anchored within myocardial tissue and flexible distal lead body portion 16 is positioned substantially outside the myocardial tissue. Lead 10 may alternatively be implanted in a partially transmural position wherein tip electrode 24 as well as at least a portion of distal lead body portion 16 and optionally flexible anode electrode 26 are implanted within the myocardial tissue. In a partially transmural implant position, stabilization member 32 is provided as a generally cylindrical piece of material positioned around the distal lead body portion 16 proximate distal lead body end 18 for promoting tissue adhesion or ingrowth.

It is recognized that a stabilization member may take a variety of configurations for promoting tissue ingrowth or adhesion for stabilizing the position of epicardial lead distal end 18. Practice of the present invention is therefore not restricted to the two examples shown in FIGS. 2 and 3, which are merely provided for illustrative purposes. It is understood that a stabilizing member may take a variety of shapes and configurations relative to distal lead body end 18 for interfacing with the tissue at the targeted implant site.

Figure 4A:
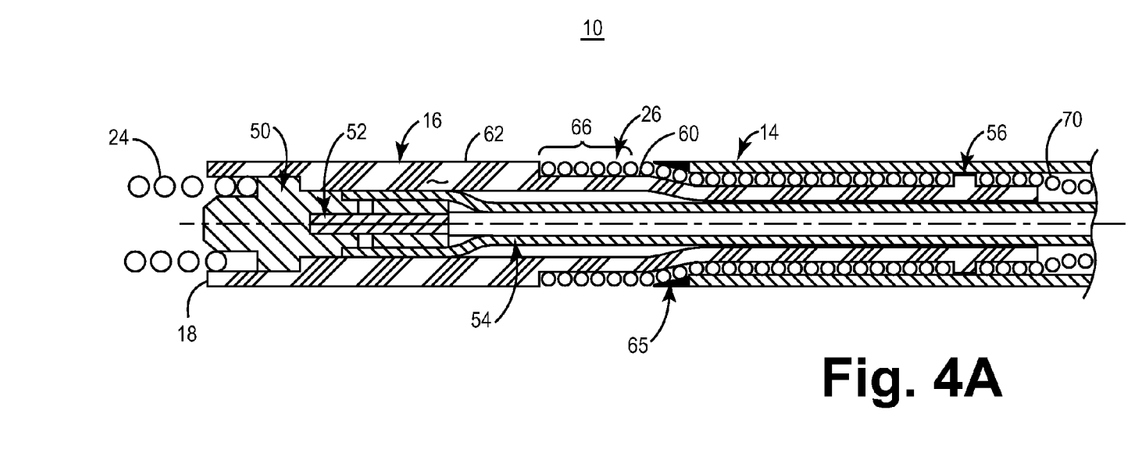
FIG. 4A is a sectional view of a distal portion of the lead shown in FIG. 1.

FIG. 4A is a sectional view of a distal portion of the cardiac lead shown in FIG. 1. Helical tip electrode 24 extends from distal lead body end 18 and is electrically coupled to cathode conductor 52 via cathode sleeve 50 by welding, crimping, staking or other appropriate method. Cathode conductor 52 may be provided, for example, in the form of a single filar or multifilar stranded, cable, fiber cored, or coiled conductor formed of a conductive metal or polymer material. An appropriate conductor for use in lead 10 is generally disclosed in U.S. Pat. No. 5,760,341 (Laske et al.), hereby incorporated herein by reference in its entirety. Conductor 52 is electrically insulated by insulating tubing 54.

Distal lead body portion 16 is formed of a flexible material such as silicone rubber and extends between distal lead body end 18 and an anode welding sleeve 56. Flexible anode electrode 26 is positioned along a portion of the outer diameter 60 of distal lead body portion 16. Distal lead body portion 16 may be provided with a variable diameter, wherein a first outer diameter 60, over which flexible anode electrode 26 is placed, is smaller than a second outer diameter 62 extending from anode electrode 26 to distal lead body end 18 such that the lead 10 is formed with a constant outer diameter.

Distal lead body portion 16 extends within the outer insulation tubing forming proximal lead body portion 14. Distal lead body portion 16 and proximal lead body portion 14 are joined at seal 65 using an adhesive. The transition between flexible distal lead body portion 16 and proximal lead body portion 14 provides a gradual transition in flexibility such that the lead body is provided with a constant or gradually changing bending stiffness. A constant bending stiffness allows the distal part of lead 10 to easily follow the contours of the beating heart without stress-induced lead fracture. A discreet change in flexibility is avoided to prevent a flexion point susceptible to fracture.

Flexible anode electrode 26 is electrically coupled to anode conductor 70 via anode sleeve 56 by welding, crimping, staking, swaging, or other appropriate method. Anode sleeve 56 is spaced proximally from the exposed portion 66 of flexible anode 26. Cathode sleeve 50 and anode sleeve 56 are relatively stiff components. In order to maintain flexibility of distal lead body portion 16, cathode sleeve 50 is kept as short as possible. Anode sleeve 56 is spaced proximally from the exposed portion 66 of flexible anode electrode 26, thereby removing anode sleeve 56 from the flexible distal lead body portion 16.

Figure 4B:
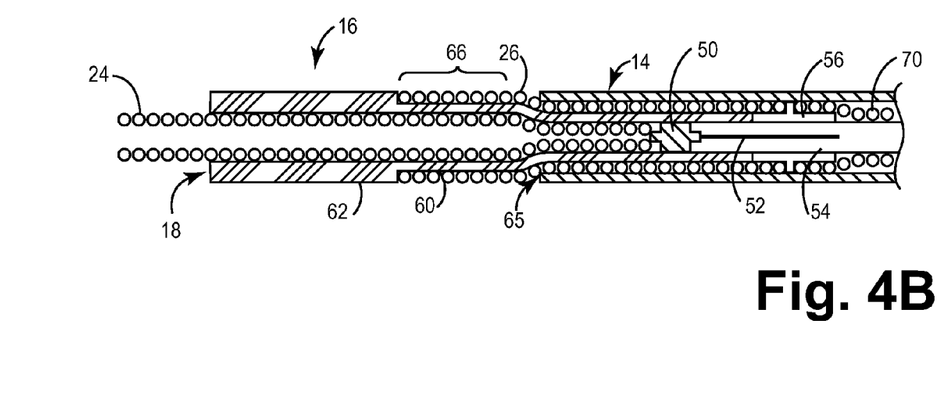
FIG. 4B is a sectional view of a distal portion of an alternative embodiment of the lead shown in FIG. 1.

FIG. 4B is a plan view of a distal portion of the cardiac lead shown in FIG. 1 wherein both the anode welding sleeve 50 and the cathode welding sleeve 56 are moved proximally from the distal lead body end 18. The windings of helical tip electrode 24 extend proximally within flexible distal portion 16 to cathode welding sleeve 50 positioned proximal to flexible distal portion 16. In still other embodiments, helical tip electrode 24 and flexible anode 26 may be formed from a platinum-iridium clad, tantalum core wire, which can eliminate the need for cathode weld sleeve 50 and anode weld sleeve 56.

Figure 5:
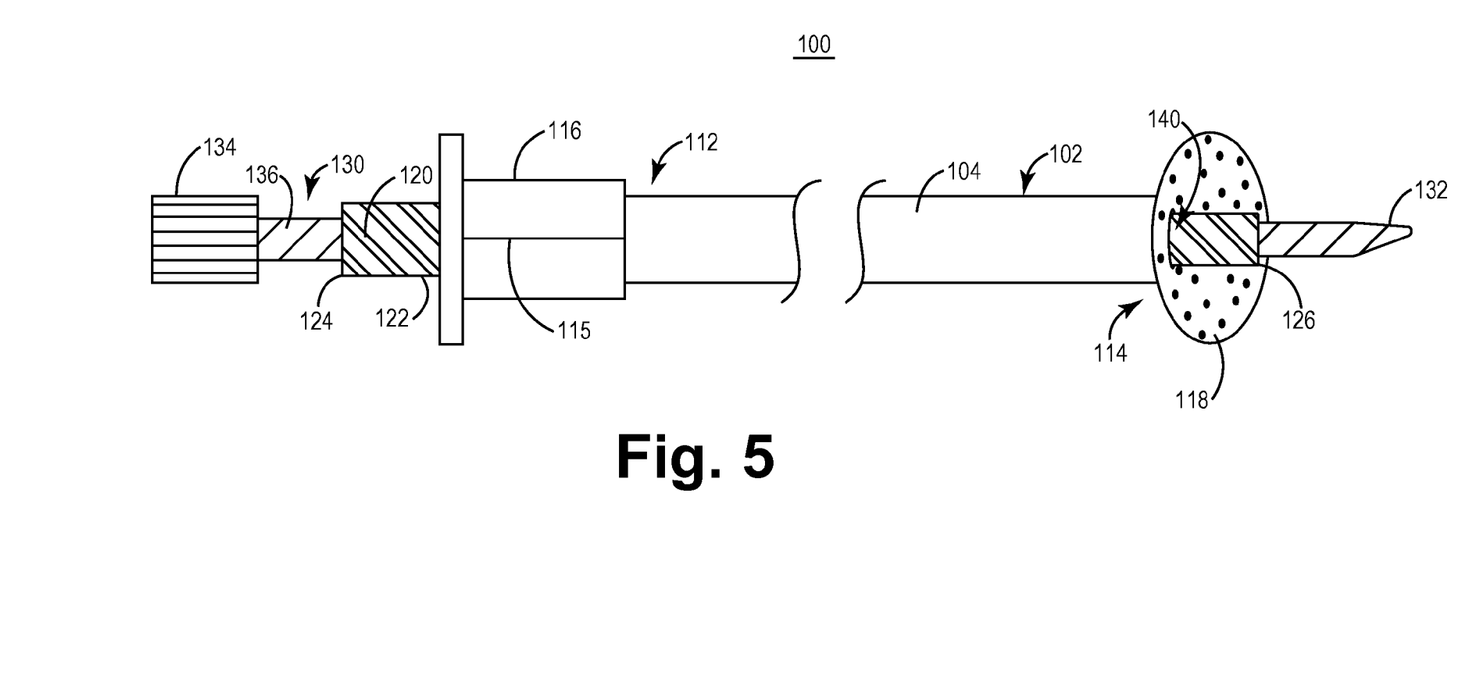
FIG. 5 is a plan view of a medical lead delivery system according to one embodiment of the invention.

FIG. 5 is a plan view of a delivery system according to one embodiment of the invention. The delivery system 100 may be used for delivering lead 10 to an epicardial implant site. In alternative embodiments, delivery system 100 may be used to delivery other devices or instruments to a targeted anatomical site. Delivery system 100 includes an outer catheter 102, an inner delivery catheter 120, and a puncture tool 130. Outer catheter 102 includes an elongated body 104 extending between a proximal end 112 and distal end 114. Elongated body 104 is typically formed from a malleable material, such as stainless steel, such that it may be shaped to a form that allows advancement of outer catheter distal end 114 to a desired location, for example on the epicardial surface of the heart. A suction device 118 is provided at outer catheter distal end 114 which is coupled to a vacuum pump for creating a suction force in the vicinity of outer catheter distal end 114. During an implant procedure, distal catheter 114 is advanced via a thoracotomy to the epicardial surface of the heart. Suction device 118 allows distal catheter end 114 to be stably positioned on the epicardial surface of the heart.

Suction device 118 includes a working port 140 in communication with the outer catheter elongated body 104. Working port 140 allows advancement of the delivery catheter 120, puncture tool 130, and epicardial lead 10 out the outer catheter distal end 114 and suction device 118. In various applications, other types of instruments, devices, or fluid agents may be delivered through working port 140.

Proximal catheter end 112 is fitted with a sealing member 116 adapted to form an air-tight seal with the outer diameter 122 of inner delivery catheter 120. When inner delivery catheter 120 is advanced through outer catheter 102 and a vacuum is applied to suction device 118, an air-tight seal between delivery catheter outer diameter 122 and sealing member 116 maintains the position of delivery catheter 120 with respect to outer catheter 102 and maintains the suction pressure applied by suction device 118 along the epicardial surface of the heart. Sealing member 116 is provided as a splittable member such that member 116 may be split open along seam 115 and removed from outer catheter 102 after epicardial lead 10 (or another device) is delivered through delivery catheter 120, as will be described in greater detail below.

Delivery catheter 120 is provided with outer diameter 122 adapted to be advanced through outer catheter 102. Delivery catheter 120 is typically formed from a flexible material such as a polyether block amide, polyurethane, or other thermoplastic elastomer. Delivery catheter 120 is adapted to receive puncture tool 130 through delivery catheter proximal end 124. Puncture tool 130 includes an elongated body 136 extending between sharpened distal tip 132 and a proximal stop 134. Proximal stop 134 is sized larger than delivery catheter outer diameter 122 such that, when puncture tool 130 is fully advanced into delivery catheter 120, proximal stop 134 interfaces with delivery catheter proximal end 124. Sharpened distal tip 132 is then extended a controlled distance outward from delivery catheter distal end 126. Delivery catheter 120 may include markings, a mechanical stop, or other feature for controlling the distance that delivery catheter 120 is advanced through outer catheter 102. Once vacuum is applied to suction device 118, sealing member 116 will act to hold delivery catheter 120 in a stable position relative to outer catheter 102.

Puncture tool 130 is provided for creating a puncture in the epicardial surface to facilitate advancement of tip electrode 24 (FIG. 1) into the epicardium. Tip electrode 24 is advanced into the epicardial surface by rotational forces applied by the implanting clinician to proximal lead body end 20, for example with the use of rotation tool 40 (FIG. 1). By creating a small epicardial puncture using puncture tool 130, tip electrode 24 is advanced more readily into the epicardium at the puncture site. Sharpened distal tip 132 is sized to create a small puncture that does not result in withdrawal of tip electrode 24. In one embodiment, sharpened distal tip 132 is ground in three planes to provide a sharp, narrow diameter tip 132. If the epicardial puncture is too large relative to the size of tip electrode 24, tip electrode 24 may readily withdraw from the myocardial tissue, which is undesirable.

Multiple puncture tools of different lengths may be provided with delivery system 100, each having different distances between proximal stop 134 and distal sharpened tip 132 such that an implanting physician may select the depth of the epicardial puncture formed using puncture tool 130. Alternatively, proximal stop 134 may be provided as a movable proximal stop that may be stably positioned at different locations along the elongated body 136 of puncture tool 130. For example, in one embodiment, proximal stop 134 is rotated to loosen proximal stop 134 such that proximal stop 134 may be moved along puncture tool body 136 to a new location. Proximal stop 134 is then rotated in an opposite direction to tighten proximal stop 134 around puncture tool body 136 to stabilize its new position along puncture tool body 136. In still other embodiments, multiple delivery catheters each having different lengths may be provided with delivery system 100 such that puncture tool sharpened tip 132 may be advanced different distances out of the differently sized delivery catheters to create different puncture depths.

In one method of use, outer catheter 102 is advanced via a thoracotomy to position outer catheter distal end 114 at a desired epicardial location, which may be over any heart chamber. Vacuum is applied to suction device 118 to stabilize the position of outer catheter distal end 114 proximate the epicardium. Delivery catheter 120 is advanced through outer catheter 102 until delivery catheter distal end 126 contacts the epicardial surface. Contact with the epicardium by distal end 126 is determined based on tactile feedback. Sealing member 116 forms an air tight seal with delivery catheter outer diameter 122. Puncture tool 130 is advanced through delivery catheter 120 until proximal stop 134 meets delivery catheter proximal end 124. Distal sharpened tip 132 will be advanced a controlled distance outward from delivery catheter distal end 126, thereby forming an epicardial puncture having a controlled depth. Note that the puncture is controlled to extend through the epicardial surface of the heart and generally does not extend all the way through the myocardium through the endocardial surface of the heart.

Puncture tool 130 is then removed from delivery catheter 120 and epicardial lead 10 (shown in FIG. 1) is advanced through delivery catheter 120. The helical tip electrode 24 is advanced into the puncture site by rotation of the proximal lead body end 20, which may be facilitated by the use of a rotation sleeve 40 (shown in FIG. 1) as described previously. It is recognized that delivery system 100 may alternatively be used for delivering other medical leads or other sensors or therapy delivery devices, such as fluid delivery devices, to a targeted body site.

Figure 6A:
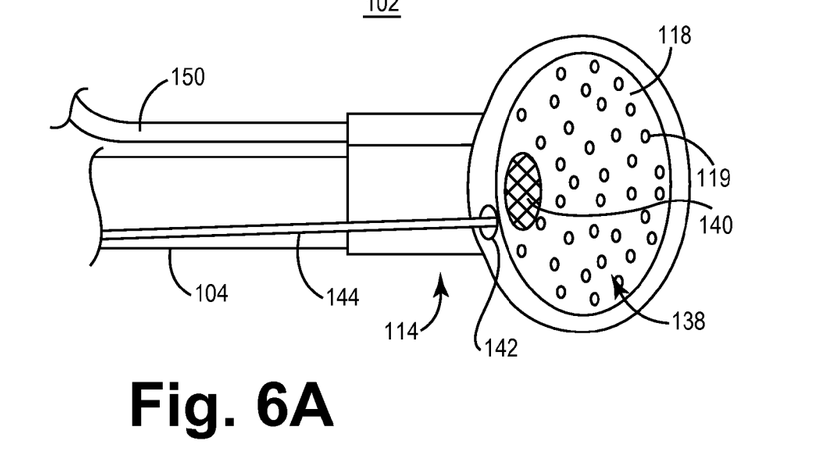
FIG. 6A is a plan view of a distal portion of the outer catheter included in the delivery system of FIG. 5.

FIG. 6A is a plan view of a distal portion of outer catheter 102. Suction device 118 is provided at distal end 114 of elongated catheter body 104. Suction device 118 is generally cup-shaped, having a plurality of suction ports 119 distributed over a concave inner surface 138 of suction device 118. A suction conduit 150 is coupled to a vacuum pump (not shown) to provide suction force distributed over suction ports 119 to form a seal between concave surface 138 and the epicardium (or other body tissue) at a target implant site. Suction device 118 temporarily immobilizes a localized area of the epicardial tissue at the target implant site and maintains a stable position of outer catheter distal end 114 at the target implant site.

Outer catheter 102 may include a distal mapping electrode 142 that is positioned proximate the epicardial tissue when suction device 118 is engaged against the epicardial surface. In the embodiment shown, mapping electrode 142 is positioned along the periphery of suction device concave surface 138. Mapping electrode 142 is electrically coupled to a conductor 144 extending to the outer catheter proximal end where it can be connected to monitoring equipment. Mapping electrode 142 can be used to sense cardiac electrogram signals or deliver a stimulation pulse to verify a selected epicardial implant site.

In alternative embodiments, a mapping electrode may be positioned at the distal end 126 of the delivery catheter 120 (shown in FIG. 5) or the distal tip 132 of the puncture tool 130 (also shown in FIG. 5). The distal tip 132 of puncture tool 130 may serve as a mapping electrode, in which case the puncture tool 130 would be provided with an insulating coating except for a portion of the distal tip 132 which remains exposed to serve as a mapping electrode. By including a mapping electrode on puncture tool distal tip 132, cardiac electrogram signals can be obtained to verify that the puncture tool distal tip 132 is within the myocardium, where and electrogram signal differs from an epicardial electrogram signal. In another embodiment, a mapping electrode instrument may be advanced through delivery catheter 120 or puncture tool 130 for performing electrophysiological measurements.

Verification of an implant site may be made electrically through the use of an electrophysiologic mapping electrode. Alternatively, an endoscope may be advanced through outer catheter 102 to provide visual verification of the catheter location for selecting an implant location. Endoscopic visualization will also provide information regarding the anatomical location of blood vessels or other anatomical structures that are preferably avoided during lead fixation.

Figure 6B:
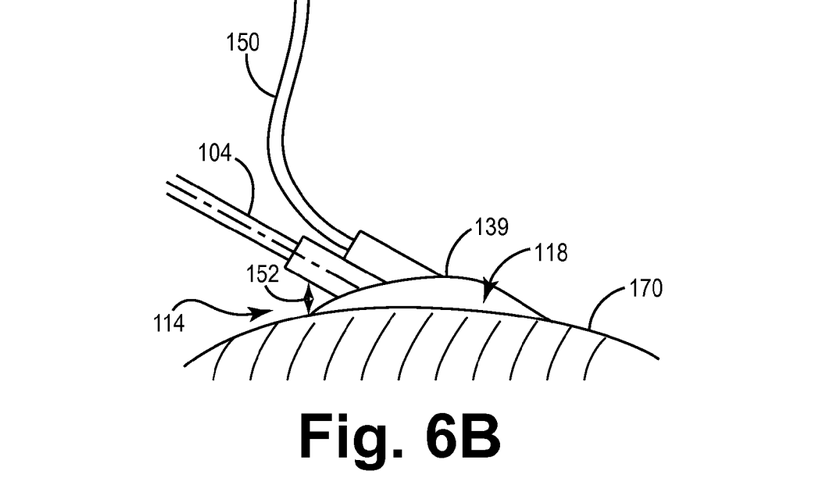
FIG. 6B is a side view of the distal portion of the outer catheter positioned against the epicardial surface of a heart.
Figure 6C:
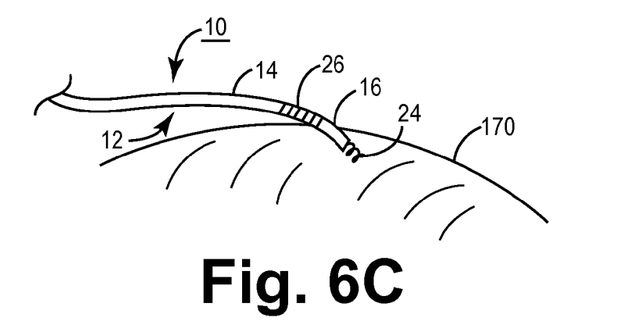
FIG. 6C is an illustration of a medical electrical lead positioned approximately tangential with the heart surface.

FIG. 6B is a side view of one embodiment of the distal outer catheter positioned against the myocardium. Distal suction device 118 may be coupled to outer catheter distal end 114 such that outer catheter body 104 extends from suction device 118 at an angle 152 relative to outer, convex surface 139 as opposed to substantially perpendicular to convex surface 139. A lead or other device delivered through outer catheter 104 will enter epicardial surface 170 at an angle. Fixation of lead 10 at an angle in the cardiac tissue, as opposed to substantially perpendicular to the epicardial surface, may provide more reliable fixation. The distal lead portion will be positioned approximately tangential with the heart wall, somewhat following the curvature of the heart wall as shown in FIG. 6C. The tangential positioning of the distal lead portion is expected to create less irritation to the surrounding tissue than a lead extending perpendicularly from the epicardium.

Suction device 118 is shown in FIG. 6B as a generally circular device having a convex outer surface, however, other shapes may be provided. Furthermore, it is to be understood that embodiments of the present invention are not limited to a particular angle between outer catheter body 104 and suction device 118. Outer catheter body 104 may extend from suction device 118 at any angle, including perpendicular, relative to outer convex surface 139.

FIG. 6C illustrates the lead 10 being positioned approximately tangential with the heart surface 170 with the distal tip electrode 24 implanted in the myocardial tissue at an angle with the epicardial surface 170. Lead body 12 is provided with a constant or gradually changing bending stiffness along flexible distal portion 16 and the transition to proximal portion 14 such that lead 10 follows the heart motion and adapts to the anatomy of the heart and surrounding tissue. Flexible anode 26 will be positioned in the epicardial tissue and/or along the epicardial surface 170.

Figure 7:
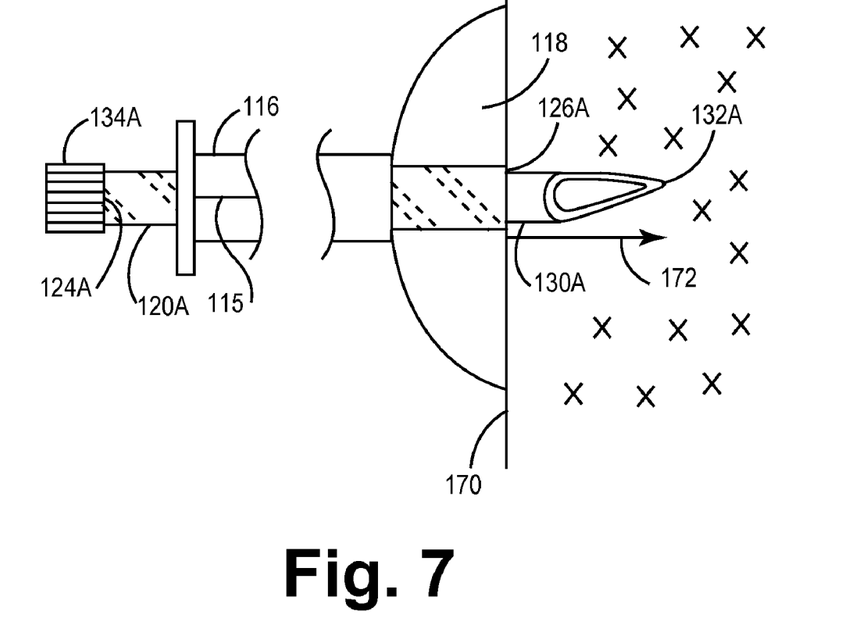
FIGS. 7 and 8 illustrate a method for implanting a lead at an epicardial implant site.
Figure 8:
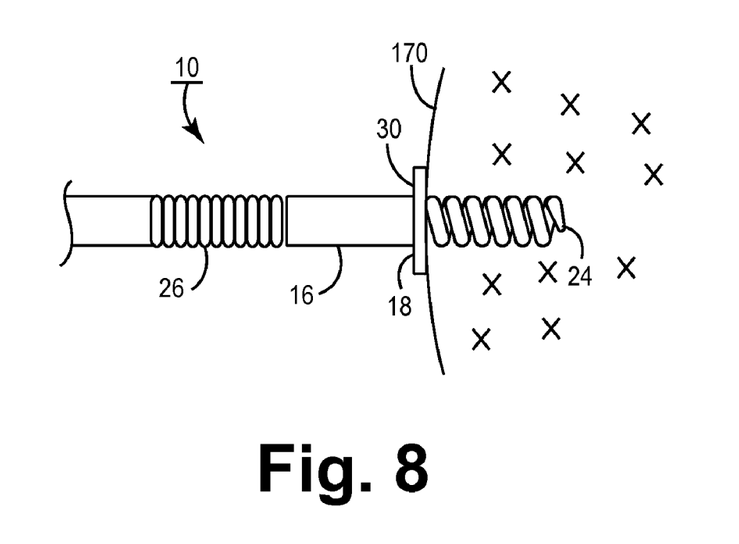

FIGS. 7 and 8 illustrate a method for implanting lead 10 in an epicardial implant site. In FIG. 7, suction device 118 and delivery catheter distal end 126A are shown positioned against an epicardial surface 170. Puncture tool 130A is fully advanced through delivery catheter 120A such that proximal stop 134A is positioned against delivery catheter proximal end 124A. Distal sharpened tip 132A of puncture tool 130A is extended through epicardial surface 170 a controlled distance 172 into the myocardial tissue.

Puncture tool 130A is then removed from delivery catheter 120A, and lead 10 is advanced through delivery catheter 120A and rotated such that tip electrode 24 is fixated in the myocardial tissue as shown in FIG. 8. The sealing member 116 is split open along seam 115 and removed. The delivery catheter 120A is removed from lead 10 either by slitting or splitting the delivery catheter 120A as it is retracted over lead body 12. Depending on the size of the delivery catheter 120A relative to lead 10, delivery catheter 120A may be removed by sliding delivery catheter 120A over proximal lead connector assembly 22 (FIG. 1). The outer catheter 102 is then removed by withdrawing it over the proximal lead connector assembly 22. Lead 10 remains implanted at the targeted epicardial site with tip-electrode 24 advanced into the myocardial tissue. Stabilization member 30 rests against the epicardial surface 170 and flexible distal lead body portion 16 and flexible anode electrode 26 remain substantially outside the myocardial tissue.

Figure 9:
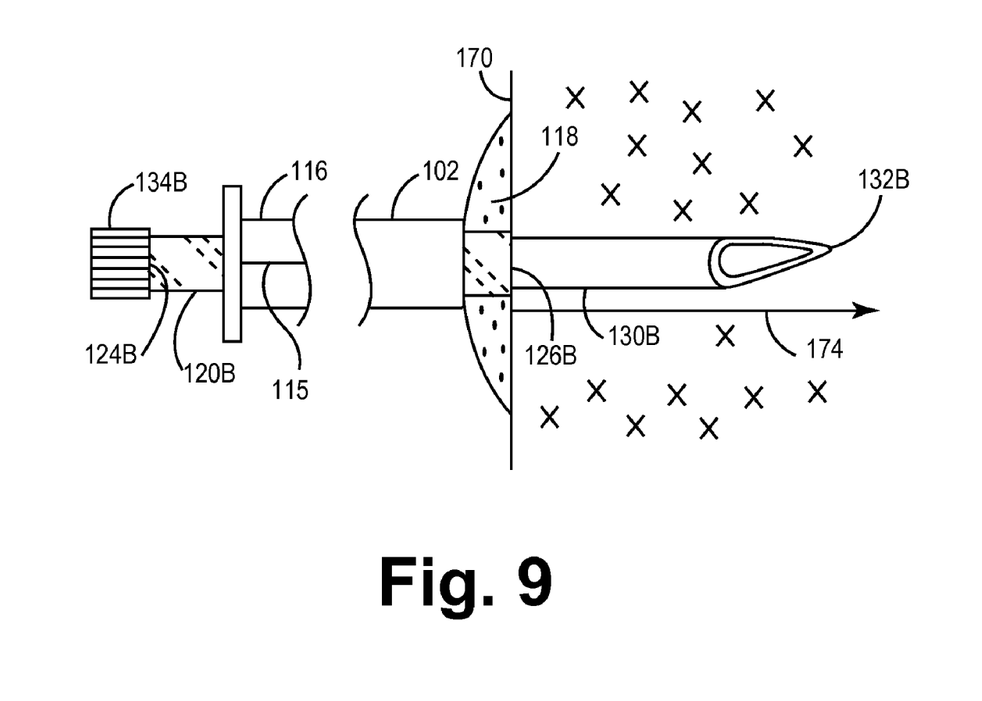
FIGS. 9 and 10 illustrate a method for implanting a lead in a partially transmural myocardial location
Figure 10:
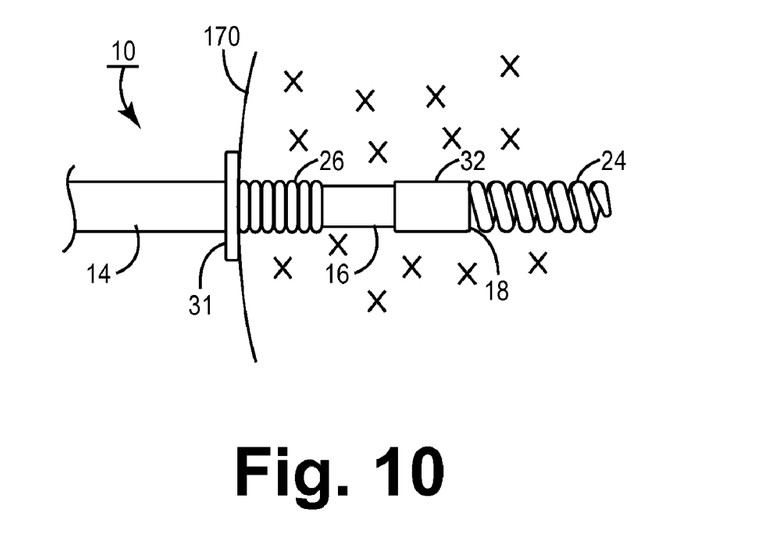

In a similar manner, lead 10 may be implanted in a partially transmural myocardial location as illustrated by FIGS. 9 and 10. In FIG. 9, a puncture tool 130B is provided having a longer distance between proximal stop 134B and distal sharpened tip 132B than puncture tool 130A. Alternatively, delivery catheter 120B is provided with a shorter distance between proximal end 124B and distal end 126B than delivery catheter 120A. Accordingly, sharpened tip 132B will extend a greater controlled distance 174 into the myocardium when proximal stop 134B is advanced to meet delivery catheter proximal end 124B when suction device 118 and delivery catheter distal end 126B are positioned against the epicardial surface 170.

After lead 10 is advanced through delivery catheter 120B and rotated so as fixate distal tip electrode 24 in the myocardium at the puncture created by puncture tool 130B. A deeper puncture is created allowing lead 10 to be implanted in the myocardium in a partially transmural configuration as shown in FIG. 10. Tip electrode 24, flexible distal lead body portion 16 and at least a portion of flexible anode 26 are shown implanted in the myocardial tissue. In this embodiment, lead 10 is fitted with a cylindrical stabilization member 32 that becomes embedded in the myocardial tissue, as described previously in conjunction with FIG. 3, and optionally a second stabilization member 31 adapted to rest against the epicardial surface 170.

Thus, a medical electrical lead and a medical lead delivery system have been presented in the foregoing description with reference to specific embodiments. It is appreciated that various modifications to the referenced embodiments may be made without departing from the scope of the invention as set forth in the following claims.

The invention claimed is:

1. A kit comprising:
  A. an electrical medical lead, comprising:
    an elongated lead body extending from a proximal end to a distal end;
    a first electrode positioned at the distal end of the lead body;
    a second electrode spaced proximally from the first electrode, the second electrode being a flexible conductive coil and having a distal end;
    a first electrode sleeve coupled to the first electrode; and
    a second electrode sleeve coupled to the second electrode and positioned within the proximal end of the lead body and proximal the distal end of the second electrode; and
  B. a delivery system for delivering the electrical medical lead, the delivery system comprising:
    an outer catheter having an elongated body extending from a proximal end to a distal end, the distal end of the outer catheter having a suction device, the suction device having a working port in communication with the outer catheter elongated body;
    an inner delivery catheter having a diameter adapted to be advanced through the outer catheter and having a proximal end into which the distal end of the lead may be inserted and having an inner lumen through which the lead may be advanced distally until the distal end of the lead extends distally from the inner delivery catheter;
    a puncture tool having a distal tip and a diameter adapted to be advanced through the inner delivery catheter until the distal tip of the puncture tool extends distally from the inner delivery catheter.

2. The kit of claim 1 wherein the first electrode comprises a fixation helix.

3. The kit of claim 2 wherein the helix is greater than two millimeters in length.

4. The kit of claim 3 wherein the helix is approximately four millimeters in length.

5. The kit of claim 2 wherein the helix is formed with a pitch of less than approximately twenty-two degrees.

6. The kit of claim 5 wherein the helix is formed with a pitch of approximately seventeen degrees.

7. The kit of claim 2 wherein the fixation helix includes an insulated proximal portion and an exposed distal portion.

8. The kit of claim 1 wherein the second electrode is provided with a low polarization coating.

9. The kit of claim 8 wherein the coating includes one of titanium nitride, platinum black, and iridium oxide.

10. The kit of claim 1 further comprising a stabilization member positioned along the distal lead body portion.

11. A kit comprising:
  A. an electrical medical lead, comprising:
    an elongated lead body extending from a proximal end to a distal end; and
    a first electrode positioned at the distal end of the lead body; and
  B. a delivery system for delivering the electrical medical lead, the delivery system comprising:
    an outer catheter having an elongated body extending from a proximal end to a distal end, the distal end of the outer catheter having a suction device, the suction device having a working port in communication with the outer catheter elongated body;
    an inner delivery catheter having a diameter adapted to be advanced through the outer catheter and having a proximal end into which the distal end of the lead may be inserted and having an inner lumen through which the lead may be advanced distally until the distal end of the lead extends distally from the inner delivery catheter;

a puncture tool having a distal tip and a diameter adapted to be advanced through the inner delivery catheter until the distal tip of the puncture tool extends distally from the inner delivery catheter.

12. The kit of claim 11 wherein the first electrode comprises a fixation helix.

13. The kit of claim 11 wherein the helix is greater than two millimeters in length.

14. The kit of claim 11 wherein the helix is formed with a pitch of less than approximately twenty-two degrees.

15. The kit of claim 11 wherein the second electrode is provided with a low polarization coating.

16. A kit comprising:

A. an electrical medical lead, comprising:

an elongated lead body extending from a proximal end to a distal end;

a first electrode positioned at the distal end of the lead body; and a second electrode spaced proximally from the first electrode, the second electrode being a flexible conductive coil and having a distal end; and B. a delivery system for delivering the electrical medical lead, the delivery system comprising:

an outer catheter having an elongated body extending from a proximal end to a distal end, the distal end of the outer catheter having a suction device, the suction device having a working port in communication with the outer catheter elongated body;

an inner delivery catheter having a diameter adapted to be advanced through the outer catheter and having a proximal end into which the distal end of the lead may be inserted and having an inner lumen through which the lead may be advanced distally until the distal end of the lead extends distally from the inner delivery catheter;

a puncture tool having a distal tip and a diameter adapted to be advanced through the inner delivery catheter until the distal tip of the puncture tool extends distally from the inner delivery catheter.

17. The kit of claim 16 wherein the first electrode comprises a fixation helix.

18. The kit of claim 16 wherein the helix is greater than two millimeters in length.

19. The kit of claim 16 wherein the helix is formed with a pitch of less than approximately twenty-two degrees.

20. The kit of claim 16 wherein the second electrode is provided with a low polarization coating.

* * * * *